United States Patent
Wondka et al.

(10) Patent No.: US 11,191,449 B2
(45) Date of Patent: Dec. 7, 2021

(54) NEONATAL CARBON DIOXIDE MEASUREMENT SYSTEM

(71) Applicant: Capnia, Inc., Redwood City, CA (US)

(72) Inventors: Anthony D. Wondka, San Ramon, CA (US); Anish Bhatnagar, Redwood City, CA (US); Pedro E. De La Serna, San Jose, CA (US)

(73) Assignee: CAPNIA, INC., Foster City, CA (US)

( * ) Notice: Subject to any disclaimer, the term of this patent is extended or adjusted under 35 U.S.C. 154(b) by 0 days.

(21) Appl. No.: 14/473,888

(22) Filed: Aug. 29, 2014

(65) Prior Publication Data

US 2015/0065900 A1     Mar. 5, 2015

Related U.S. Application Data

(60) Provisional application No. 61/872,415, filed on Aug. 30, 2013.

(51) Int. Cl.
*A61B 5/083* (2006.01)
*A61B 5/08* (2006.01)
*A61B 5/097* (2006.01)
*G01N 33/497* (2006.01)

(52) U.S. Cl.
CPC .......... *A61B 5/0836* (2013.01); *A61B 5/0816* (2013.01); *A61B 5/097* (2013.01); *G01N 33/497* (2013.01)

(58) Field of Classification Search
None
See application file for complete search history.

(56) References Cited

U.S. PATENT DOCUMENTS

| | | |
|---|---|---|
| 2,073,192 A | 3/1937 | Connell |
| 3,306,283 A | 2/1967 | Arp |
| 3,343,529 A | 9/1967 | Miller et al. |
| 3,858,573 A | 1/1975 | Ryan et al. |
| 3,910,261 A | 10/1975 | Ragsdale et al. |
| 3,923,043 A | 12/1975 | Yanda |
| 4,440,177 A | 4/1984 | Anderson et al. |
| 4,619,269 A | 10/1986 | Cutlet et al. |

(Continued)

FOREIGN PATENT DOCUMENTS

| | | |
|---|---|---|
| CN | 1097120 A | 1/1995 |
| CN | 1767785 A | 5/2006 |

(Continued)

OTHER PUBLICATIONS

Bartlett et al, Maximtim Breathing Capacity With Various Expiratory and Inspiratory Resistances (Single and Combined) at Various Breathing Rates, 1957.*

(Continued)

*Primary Examiner* — Kaylee R Wilson
*Assistant Examiner* — Jay B Shah
(74) *Attorney, Agent, or Firm* — Cooley LLP

(57) ABSTRACT

A breath parameter measuring device is described which takes into account breathing patterns which historically have been incompatible with accurate measurements. In particular, during fast breathing patterns, the sensor performing the measurement may not be able to respond quickly enough to provide the true reading. The disclosure may be useful for example in the case of neonatal breath carbon dioxide measurements.

19 Claims, 6 Drawing Sheets

(56) References Cited

U.S. PATENT DOCUMENTS

| | | | |
|---|---|---|---|
| 4,671,298 A | 6/1987 | Babb et al. |
| 5,003,985 A | 4/1991 | White et al. |
| 5,050,615 A | 9/1991 | Malkamaki |
| 5,069,220 A | 12/1991 | Casparie et al. |
| 5,072,737 A | 12/1991 | Goulding |
| 5,129,401 A | 7/1992 | Corenman et al. |
| 5,285,794 A | 2/1994 | Lynch |
| 5,357,971 A | 10/1994 | Sheehan et al. |
| 5,361,771 A | 11/1994 | Craine et al. |
| 5,361,772 A | 11/1994 | Murnick et al. |
| 5,363,857 A | 11/1994 | Howard |
| 5,383,469 A | 1/1995 | Vreman et al. |
| 5,474,062 A | 12/1995 | DeVries et al. |
| 5,533,512 A | 7/1996 | Novotny et al. |
| 5,533,513 A | 7/1996 | Ueda et al. |
| 5,573,005 A | 11/1996 | Ueda et al. |
| 5,787,885 A | 8/1998 | Lemelson |
| 5,924,995 A | 7/1999 | Klein et al. |
| 5,971,934 A | 10/1999 | Scherer et al. |
| 6,010,459 A | 1/2000 | Silkoff et al. |
| 6,038,913 A | 3/2000 | Gustafsson et al. |
| 6,251,082 B1 | 6/2001 | Rayburn |
| 6,278,975 B1 | 8/2001 | Brant et al. |
| 6,428,483 B1 | 8/2002 | Carlebach |
| 6,544,190 B1 | 4/2003 | Smits et al. |
| 6,582,376 B2 | 6/2003 | Baghdassarian |
| 6,620,107 B2 | 9/2003 | Payne et al. |
| 6,733,463 B2 | 5/2004 | Moilanen et al. |
| 6,739,335 B1 | 5/2004 | Rapport et al. |
| 6,799,575 B1 | 10/2004 | Carter |
| 6,884,222 B1 | 4/2005 | Braig |
| 7,063,667 B1 | 6/2006 | Ben-Oren et al. |
| 7,076,371 B2 | 7/2006 | Fu |
| 7,191,000 B2 | 3/2007 | Zhu et al. |
| 7,192,782 B2 | 3/2007 | Roller et al. |
| 7,223,244 B1 | 5/2007 | Koh |
| 7,600,439 B1 | 10/2009 | Patterson et al. |
| 7,775,210 B2 | 8/2010 | Schobel (nee Bauer) et al. |
| 7,814,906 B2 | 10/2010 | Moretti |
| 8,021,308 B2 | 9/2011 | Capnia |
| 8,251,914 B2 | 8/2012 | Daniels et al. |
| 8,485,984 B2 | 7/2013 | Giron et al. |
| 8,672,852 B2 | 3/2014 | Gavish |
| 8,679,029 B2 | 3/2014 | Krauss et al. |
| 9,095,534 B2 | 8/2015 | Stenzler et al. |
| 9,541,497 B2 | 1/2017 | Heyne et al. |
| 9,655,543 B2 | 5/2017 | Aoki et al. |
| 10,034,621 B2 | 7/2018 | Wondka et al. |
| 10,499,819 B2 | 12/2019 | Wondka et al. |
| 11,058,324 B2 | 7/2021 | Wondka et al. |
| 2001/0037070 A1 | 11/2001 | Cranley et al. |
| 2002/0005197 A1 | 1/2002 | DeVries et al. |
| 2002/0095096 A1 | 7/2002 | Mault |
| 2002/0138213 A1 | 9/2002 | Mault |
| 2002/0151814 A1 | 10/2002 | Payne et al. |
| 2003/0008407 A1 | 1/2003 | Fu |
| 2003/0109795 A1 | 6/2003 | Webber |
| 2003/0134427 A1 | 7/2003 | Roller et al. |
| 2003/0191405 A1 | 10/2003 | Rich et al. |
| 2003/0208133 A1 | 11/2003 | Mault |
| 2003/0216660 A1 | 11/2003 | Ben-Oren et al. |
| 2004/0077995 A1 | 4/2004 | Ferek-Petric et al. |
| 2004/0210154 A1 | 10/2004 | Kline |
| 2005/0137491 A1 | 6/2005 | Paz et al. |
| 2005/0153346 A1 | 7/2005 | Scheider |
| 2005/0177056 A1 | 8/2005 | Giron et al. |
| 2006/0094964 A1 | 5/2006 | Ragauskas et al. |
| 2006/0133960 A1 | 6/2006 | Ahmad |
| 2006/0178592 A1 | 8/2006 | Nason et al. |
| 2006/0195040 A1 | 8/2006 | Nason et al. |
| 2006/0200037 A1 | 9/2006 | Falasco |
| 2006/0241507 A1 | 10/2006 | Carlson et al. |
| 2006/0253045 A1 | 11/2006 | Coifman |
| 2007/0016092 A1 | 1/2007 | Shaw et al. |
| 2007/0073182 A1 | 3/2007 | Wilson |
| 2007/0129647 A1* | 6/2007 | Lynn | A61B 5/00 600/538 |
| 2007/0144518 A1* | 6/2007 | Acker | A61M 16/085 128/204.21 |
| 2007/0155208 A1 | 7/2007 | Pirzada |
| 2007/0167853 A1 | 7/2007 | Melker et al. |
| 2007/0173731 A1 | 7/2007 | Meka et al. |
| 2007/0179395 A1 | 8/2007 | Sotos et al. |
| 2007/0213620 A1 | 9/2007 | Reisfeld |
| 2007/0213624 A1 | 9/2007 | Reisfeld et al. |
| 2007/0232950 A1 | 10/2007 | West |
| 2007/0261472 A1 | 11/2007 | Flaherty et al. |
| 2008/0009762 A1 | 1/2008 | Hampton et al. |
| 2008/0038154 A1 | 2/2008 | Longbottom et al. |
| 2008/0119753 A1 | 5/2008 | Ricciardelli et al. |
| 2008/0119754 A1 | 5/2008 | Hietala |
| 2008/0121230 A1 | 5/2008 | Cortez et al. |
| 2008/0221471 A1 | 9/2008 | Djupesland et al. |
| 2008/0289628 A1 | 11/2008 | Hallback et al. |
| 2009/0044805 A1 | 2/2009 | Somaiya et al. |
| 2009/0054799 A1 | 2/2009 | Vrtis et al. |
| 2009/0187113 A1 | 7/2009 | Friedman et al. |
| 2009/0246891 A1 | 10/2009 | Sato et al. |
| 2009/0247891 A1 | 10/2009 | Wood |
| 2010/0268106 A1 | 10/2010 | Johnson et al. |
| 2010/0317986 A1 | 12/2010 | Colman et al. |
| 2011/0004108 A1 | 1/2011 | Peyton |
| 2011/0021942 A1 | 1/2011 | Choe et al. |
| 2011/0066060 A1 | 3/2011 | Von Bahr et al. |
| 2011/0196295 A1 | 8/2011 | Gonzalez et al. |
| 2011/0257550 A1 | 10/2011 | Choi |
| 2011/0263947 A1 | 10/2011 | Utley et al. |
| 2012/0055481 A1 | 3/2012 | Orr et al. |
| 2012/0090378 A1 | 4/2012 | Wang et al. |
| 2012/0101400 A1 | 4/2012 | Kurosawa et al. |
| 2012/0215125 A1 | 8/2012 | Orr et al. |
| 2012/0247471 A1 | 10/2012 | Masic et al. |
| 2012/0302908 A1 | 11/2012 | Hemnes et al. |
| 2012/0310104 A1 | 12/2012 | Van Kesteren et al. |
| 2013/0165806 A1 | 6/2013 | Wondka et al. |
| 2013/0217029 A1 | 8/2013 | Sislian et al. |
| 2013/0253360 A1 | 9/2013 | Wang et al. |
| 2013/0267862 A1 | 10/2013 | Jaffe et al. |
| 2013/0331723 A1 | 12/2013 | Hernandez-Silveira et al. |
| 2014/0194703 A1 | 7/2014 | Wondka et al. |
| 2014/0228699 A1* | 8/2014 | Causevic | A61B 5/083 600/532 |
| 2014/0275857 A1 | 9/2014 | Toth et al. |
| 2015/0065901 A1 | 3/2015 | Bhatnagar et al. |
| 2015/0265184 A1 | 9/2015 | Wondka et al. |
| 2016/0106343 A1 | 4/2016 | Wondka et al. |
| 2019/0024632 A1 | 1/2019 | Causevic et al. |
| 2019/0029547 A1 | 1/2019 | Watarai et al. |
| 2019/0142303 A1 | 5/2019 | Wondka et al. |
| 2019/0175067 A1 | 6/2019 | Wondka et al. |
| 2020/0046254 A1 | 2/2020 | Wondka et al. |
| 2020/0305729 A1 | 10/2020 | Wondka et al. |

FOREIGN PATENT DOCUMENTS

| | | |
|---|---|---|
| CN | 1895691 A | 1/2007 |
| CN | 1926427 A | 3/2007 |
| CN | 1950120 A | 4/2007 |
| CN | 101026995 A | 8/2007 |
| CN | 101098726 A | 1/2008 |
| CN | 101153840 A | 4/2008 |
| CN | 101214151 A | 7/2008 |
| CN | 101340941 A | 1/2009 |
| CN | 101366672 A | 2/2009 |
| CN | 101547716 A | 9/2009 |
| CN | 101636109 A | 1/2010 |
| CN | 101657710 A | 2/2010 |
| CN | 201692453 U | 1/2011 |
| CN | 201727541 U | 2/2011 |
| CN | 102188241 A | 9/2011 |
| CN | 102711605 A | 10/2012 |
| CN | 102770069 A | 11/2012 |
| CN | 103379855 A | 10/2013 |
| EP | 0 574 027 A2 | 12/1993 |

(56) References Cited

FOREIGN PATENT DOCUMENTS

| | | |
|---|---|---|
| EP | 0 648 088 A1 | 4/1995 |
| EP | 1 480 557 | 12/2004 |
| EP | 0892926 | 12/2006 |
| EP | 2 066 236 A2 | 6/2009 |
| EP | 2293056 | 3/2011 |
| EP | 1850748 | 8/2011 |
| GB | 2 472 116 A | 1/2011 |
| JP | S-49-009085 A | 1/1974 |
| JP | S-61-100231 A | 5/1986 |
| JP | H-05-337102 A | 12/1993 |
| JP | 6-58919 A | 3/1994 |
| JP | H-7-116145 A | 5/1995 |
| JP | H-7-284488 A | 10/1995 |
| JP | A-11-160311 A | 6/1999 |
| JP | 2000-506601 A | 5/2000 |
| JP | 2001-502222 A | 2/2001 |
| JP | 2001-516875 A | 10/2001 |
| JP | 2003-505180 A | 2/2003 |
| JP | 2003-529044 A | 9/2003 |
| JP | 2003-529766 A | 10/2003 |
| JP | 2005-519272 A | 6/2005 |
| JP | A-2008-530532 A | 8/2008 |
| JP | 2009-058398 A | 3/2009 |
| JP | 2009-545408 A | 12/2009 |
| JP | 2010-233611 A | 10/2010 |
| JP | 2013-519896 A | 5/2013 |
| JP | 2015-502830 A | 1/2015 |
| JP | 2015-503962 A | 2/2015 |
| WO | WO-97/43952 A1 | 11/1997 |
| WO | WO-98/43539 A1 | 10/1998 |
| WO | WO-97/38307 A1 | 5/2000 |
| WO | WO-00/063683 A1 | 10/2000 |
| WO | WO-03/073935 A2 | 9/2003 |
| WO | WO-03/073935 A3 | 9/2003 |
| WO | WG-2004/032719 A2 | 4/2004 |
| WO | WO-2004/032719 A3 | 4/2004 |
| WO | WO-2005/088289 A1 | 9/2005 |
| WO | WO-2006/086323 A1 | 8/2006 |
| WO | WO-2007/059263 A2 | 5/2007 |
| WO | WO-2007/059263 A3 | 5/2007 |
| WO | WO-2008/019294 A2 | 2/2008 |
| WO | WO-2008/019294 A3 | 2/2008 |
| WO | WO-2008/019680 A2 | 2/2008 |
| WO | WO-2008/019680 A3 | 2/2008 |
| WO | WO-2008/060165 A1 | 5/2008 |
| WO | WO-2008/081449 A2 | 7/2008 |
| WO | WO-2008/081449 A3 | 7/2008 |
| WO | WO-2008/112927 A2 | 9/2008 |
| WO | WO-2008/112927 A3 | 9/2008 |
| WO | WO-2010/097716 A1 | 9/2010 |
| WO | WO-2011/055250 A2 | 5/2011 |
| WO | WO-2011/055250 A3 | 5/2011 |
| WO | WO 2011055250 A2 * | 5/2011 ........... A61B 5/0816 |
| WO | WO-2011/070472 A1 | 6/2011 |
| WO | WO-2011/101776 A1 | 8/2011 |
| WO | WO-2012/053910 | 4/2012 |
| WO | WO-2012/059768 | 5/2012 |
| WO | WO-2012/076614 | 6/2012 |
| WO | WO-2012/146991 A1 | 11/2012 |
| WO | WO-2013/003429 A1 | 1/2013 |
| WO | WO-2013/095284 A1 | 6/2013 |
| WO | WO-2013/096695 A2 | 6/2013 |
| WO | WO-2013/096695 A3 | 6/2013 |
| WO | WO-2014/110181 A1 | 7/2014 |
| WO | WO-2014/127044 A1 | 8/2014 |
| WO | WO-2015/031848 A2 | 3/2015 |
| WO | WO-2015/031848 A3 | 3/2015 |
| WO | WO-2015/031850 A1 | 3/2015 |
| WO | WO-2015/143384 A1 | 9/2015 |
| WO | WO-2016/064925 A1 | 4/2016 |
| WO | WO-2017/130646 A1 | 8/2017 |

OTHER PUBLICATIONS

Jaffe, Mainstream or Sidestream Capnography?—White Paper, 2002.*
International Search Report and Written Opinion for PCT/US12/71085, dated May 13, 2013, 10 pages.
International Search Report and Written Opinion for PCT/US14/10746, dated Apr. 15, 2014, 8 pages.
International Search Report and Written Opinion for PCT/US2014/016105, dated Apr. 30, 2014, 7 pages.
International Search Report and Written Opinion for PCT/US2014/053567 dated Dec. 18, 2014, 15 pages.
International Search Report and Written Opinion for PCT/US14/53572, dated Dec. 24, 2014, 8 pages.
Medtronic Capnography brochure MIN 3012492-001 /CAT 21300-001569.
Molloy et al., "Are carbon dioxide detectors useful in neonates?" Arch Dis Child Fetal Neonatal Ed (2006) 91:F295-F298.
International Search Report and Written Opinion for PCT/US14/53569, dated Feb. 17, 2015, 18 pages.
Extended European Search Report dated Feb. 26, 2016, for European Patent Application No. 12 860 711.6, filed on Dec. 20, 2012, 6 pages.
Extended European Search Report dated Jun. 8, 2016, for European Patent Application No. 14 737 690.9, filed on Jan. 8, 2014, 9 pages.
Extended European Search Report dated Sep. 30, 2016, for European Patent Application No. 14 751 436.8, filed on Feb. 12, 2014, 8 pages.
Extended European Search Report dated Mar. 16, 2017, for European Patent Application No. 14 839 697.1, filed on Aug. 29, 2014, 9 pages.
Final Office Action dated Aug. 24, 2016, for U.S. Appl. No. 13/722,950, filed Dec. 20, 2012, 11 pages.
Final Office Action dated Mar. 21, 2017, for U.S. Appl. No. 14/150,625, filed Jan. 8, 2014, 14 pages.
International Search Report dated Jul. 2, 2015, for PCT Application No. PCT/US2015/021852, filed on Mar. 20, 2015, 2 pages.
International Search Report dated Feb. 9, 2016, for PCT Application No. PCT/US2015/056527, filed on Oct. 20, 2015, 4 pages.
Non-Final Office Action dated Dec. 1, 2015, for U.S. Appl. No. 13/722,950, filed Dec. 20, 2012, 7 pages.
Non-Final Office Action dated Dec. 18, 2015, for U.S. Appl. No. 14/150,625, filed Jan. 8, 2014, 13 pages.
Non-Final Office Action dated Nov. 10, 2016, for U.S. Appl. No. 14/179,381, filed Feb. 12, 2014, 12 pages.
Non-Final Office Action dated Mar. 13, 2017, for U.S. Appl. No. 13/722,950, filed Dec. 20, 2012, 7 pages.
Non-Final Office Action dated Mar. 23, 2017, for U.S. Appl. No. 14/664,728, filed Mar. 20, 2015, 18 pages.
Non-Final Office Action dated Apr. 20, 2017, for U.S. Appl. No. 14/473,878, filed Aug. 29, 2014, 10 pages.
Written Opinion of the International Searching Authority dated May 13, 2013, for PCT Application No. PCT/US2012/071085, filed on Dec. 20, 2012, 6 pages.
Written Opinion of the International Searching Authority dated Apr. 15, 2014, for PCT Application No. PCT/US2014/010746, filed on Jan. 8, 2014, 6 pages.
Written Opinion of the International Searching Authority dated Apr. 30, 2014, for PCT Application No. PCT/US2014/016105, filed on Feb. 12, 2014, 5 pages.
Written Opinion of the International Searching Authority dated Feb. 17, 2015, for PCT Application No. PCT/US2014/053569, filed on Aug. 29, 2014, 6 pages.
Written Opinion of the International Searching Authority dated Dec. 18, 2014, for PCT Application No. PCT/US2014/053567, filed on Aug. 29, 2014, 5 pages.
Written Opinion of the International Searching Authority dated Dec. 24, 2014, for PCT Application No. PCT/US2014/053572, filed on Aug. 29, 2014, 5 pages.
Written Opinion of the International Searching Authority dated Jul. 2, 2015, for PCT Application No. PCT/US2015/021852, filed on Mar. 20, 2015, 8 pages.
Written Opinion of the International Searching Authority dated Feb. 9, 2016, for PCT Application No. PCT/US2015/056527, filed on Oct. 20, 2015, 6 pages.

(56) References Cited

OTHER PUBLICATIONS

Extended European Search Report dated Jul. 12, 2017, for European Patent Application No. 14 838 958.8, filed on Aug. 29, 2014, 11 pages.
Extended European Search Report dated Oct. 16, 2017, for European Patent Application No. 15 764 503.7, filed on Mar. 20, 2015, 8 pages.
Final Office Action dated Aug. 16, 2017, for U.S. Appl. No. 14/179,381, filed Feb. 12, 2014, 11 pages.
Final Office Action dated Oct. 19, 2017, for U.S. Appl. No. 14/664,728, filed Mar. 20, 2015, 18 pages.
Final Office Action dated Nov. 20, 2017, for U.S. Appl. No. 14/473,878, filed Aug. 29, 2014, 11 pages.
Partial Supplementary European Search Report dated Apr. 7, 2017, for European Patent Application No. 14 838 958.8, filed on Aug. 29, 2014, 7 pages.
Coburn, R.F. et al. (1966). "Endogenous Carbon Monoxide Production in Patients with Hemolytic Anemia," Journal of Clinical Investigation 45:460-468.
Ebola Virus Infection (2017). Doctor-clinic.org, 2 total pages.
Final Office Action dated Dec. 29, 2017, for U.S. Appl. No. 13/722,950, filed Dec. 20, 2012, 5 pages.
Final Office Action dated Jun. 5, 2018, for U.S. Appl. No. 14/473,878, filed Aug. 29, 2014, 10 pages.
Non-Final Office Action dated Dec. 15, 2017, for U.S. Appl. No. 14/918,484, filed Oct. 20, 2015, 15 pages.
Non-Final Office Action dated Jan. 9, 2018, for U.S. Appl. No. 14/150,625, filed Jan. 8, 2014, 8 pages.
Notice of Allowance dated Mar. 30, 2018, for U.S. Appl. No. 13/722,950, filed Dec. 20, 2012, 7 pages.
Final Office Action dated Nov. 9, 2018, for U.S. Appl. No. 14/150,625, filed Jan. 8, 2014, 7 pages.
Non-Final Office Action dated Oct. 18, 2018, for U.S. Appl. No. 14/664,728, filed Mar. 20, 2015, 23 pages.
Non-Final Office Action dated Jan. 10, 2019, for U.S. Appl. No. 14/473,878, filed Aug. 29, 2014, 9 pages.
RESTEK Product catalog 2011/2012 https://www.calameo.com/books/00004252746f79e5d8c85 (Year: 2012), 1 total page.
Final Office Action dated Nov. 1, 2019, for U.S. Appl. No. 14/473,878, filed Aug. 29, 2014, 8 pages.
Notice of Allowance dated Aug. 12, 2019, for U.S. Appl. No. 14/150,625, filed Jan. 8, 2014, 8 pages.
Non-Final Office Action dated Apr. 29, 2020, for U.S. Appl. No. 14/473,878, filed Aug. 29, 2014, 9 pages.
Non-Final Office Action dated Sep. 3, 2020, for U.S. Appl. No. 16/044,902, filed Jul. 25, 2018, 9 pages.
Non-Final Office Action dated Oct. 14, 2020, for U.S. Appl. No. 15/897,606, filed Feb. 15, 2018, 9 pages.
Final Office Action dated Feb. 2, 2021, for U.S. Appl. No. 14/473,878, filed Aug. 29, 2014, 12 pages.
Non-Final Office Action dated Jan. 6, 2021, for U.S. Appl. No. 16/008,594, filed Jun. 14, 2018, 14 pages.
Non-Final Office Action dated Mar. 24, 2021, for U.S. Appl. No. 16/386,034, filed Apr. 16, 2019, 25 pages.
Non-Final Office Action dated May 14, 2021, for U.S. Appl. No. 15/897,606, filed Feb. 15, 2018, 10 pages.
Notice of Allowance dated Mar. 15, 2021, for U.S. Appl. No. 16/044,902, filed Jul. 25, 2018, 7 pages.
Sanchez, A. (2004). "Analysis of Human Peripheral Blood Samples from Fatal and Nonfatal Cases of Ebola (Sudan) Hemorrhagic Fever: Cellular Responses, Virus Load, and Nitric Oxide Levels," J. Viral. 78:10370-10377.

* cited by examiner ( Prior Art )

NEONATAL CARBON DIOXIDE MEASUREMENT SYSTEM

CROSS-REFERENCE TO RELATED APPLICATION

This application claims the benefit of U.S. Provisional Application No. 61/872,415, filed Aug. 30, 2013, the content of which is incorporated herein in its entirety.

FIELD OF THE INVENTION

The present Disclosure applies to the field of breath measurements and monitoring and specifically to the field of measuring a constituent in the exhaled gas of a patient for the purpose of monitoring the patient's condition.

BACKGROUND

In various breath parameter measurement applications, the current state-of-the-art measurement technology may not provide an accurate or reliable measurement during fast breathing patterns because the response time of the sensor employed is not fast enough to measure the breath parameter. Such measurement applications may be those in which continuous monitoring is desired, or in which intermittent monitoring is desired, or in which a one-time breath test is desired. In capnometery for example, Infra-Red sensors are used to measure the CO2 in the exhaled breath. The sensor can be in line with the patient's exhaled gas stream, or coupled to the exhaled gas stream through a gas sample scavenging tube, typically referred to as a sampling line in the case of mechanical ventilation or a nasal cannula in the case of spontaneous breathing. With fast breathing patterns the capnometry sensor is usually capable of registering a breath rate, since a waveform of some amplitude is registered for each breath, however, the sensor is not capable of registering a true peak value of CO2 for each breath. A review of the product literature available for commercial systems indicates that this limitation does indeed exist.

BRIEF SUMMARY

In current capnometry systems, especially neonatal capnometry, there are two main technical limitations that prevent accurate measurements. First, the breath sample collection apparatus allows mixing of one section of gas with another section of gas, thus disturbing the homogeneity and purity of the different and discrete sections. This mixing occurs in the patient interface components, valves, filters, water traps, the breath sensor itself, connectors and the sampling tubing. A solution to this technical problem has been described by Capnia (Reference: Capnia U.S. Provisional Patent Application No. 61/872,270, the entire contents of which are incorporated herein). The second problem, which is addressed in the present disclosure, is the intrinsic response time of the sensor technology being employed. This response time of the sensor is not fast enough to accurately measure the CO2 in a breath when the patient is breathing fast, such as greater than 30 breaths per minute (bpm). Gas obtained from the patient travels through the sensor. When expiratory gas is flowing through the sensor, the sensor will respond to the CO2 molecules in the gas, this response known as the signal response. The amplitude of the signal response depends on and corresponds to the amount of CO2 molecules or CO2 concentration in the gas sample. However the sensor signal response is not instantaneous; it can take as long as 400 milliseconds (ms) for the sensor to finish responding to the CO2 molecules in a bolus of gas from a single expiratory cycle. Therefore, if the patient transitions from exhalation to inspiration before the sensor has finished responding to the CO2 molecules in the expiratory gas bolus, the sensor's signal response will not reach the true peak value. This technical problem is called clipping of the signal. Designers can try to extrapolate where the signal would have peaked had the sensor been fast enough, but these extrapolations are inexact, don't take into account the prevailing clinical conditions of the patient, and should not be used in a medical breath test application. An example of this response time limitation follows.

Assuming a patient is breathing at 60 bpm, with a 50/50 Inspiratory/Expiratory time ratio his or her expiratory time will be 500 ms. Assuming the lung is 50% airway deadspace, and assuming a constant expiratory flow rate, the person will expire alveolar gas for half of the expiratory time, or for 250 ms. Now, assuming the sensor has a response time of 300 milliseconds, at the end of exhalation, the sensor will have not fully responded to all of the CO2 molecules in the bolus of alveolar gas, and will have reached only 83% of the true peak value (250/300), assuming the signal response is linear. This means that the sensor signal gets truncated before it reaches the true amplitude of the gas being measured, and in this example may read for 4% CO2 instead of 5% CO2. For these above reasons, it is known in the medical community, that capnometry cannot be relied upon for neonatal CO2 monitoring, unless the patient is breathing below 40 or 50 bpm, which often does not occur depending on the patient's age and condition. Some manufacturers of capnometry monitors often state that the device is not for neonatal use for this reason.

There are some potential options to circumvent the limitation described above. First, CO2 can be measured in the blood, however, this is invasive and therefore is not a preferred test and is not used for continuous monitoring or repeat testing. Second, CO2 can be measured transcutaneously, but these systems have not yet been proven to be reliable in all clinical situations. (See Arch Dis Child Fetal Neonatal Ed. 2006 July; 91(4): F295-F298. Are carbon dioxide detectors useful in neonates? E J Molloy and K Deakins.)

Because there is a clinical need for neonatal CO2 measurements, and because of the overwhelming desire for this measurement to be non-invasive and the desire to have the option of continuous or intermittent monitoring, there is a significant unmet need for an accurate, reliable Capnometer for this patient population and other clinical situations and populations in which breathing frequency is relatively fast compared to the sensor being employed.

It should be noted again that while the disclosure is described for the most part in terms of neonatal capnometry, the same disclosure applies to other breath markers such as O2, and clinical applications other than neonates.

DETAILED DESCRIPTION OF THE INVENTION

Figure 1:
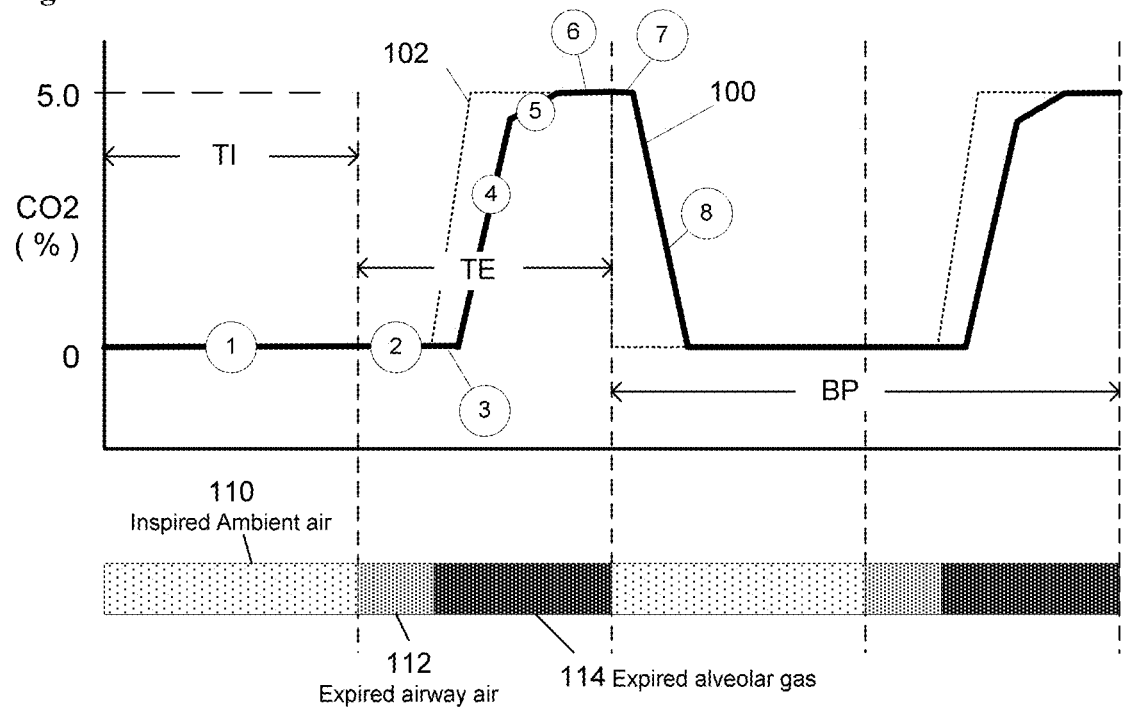
FIG. 1 describes capnometry prior art with a CO2 value in the breath measured as a function of time.

FIG. 1 graphically describes capnometry, when used for non-infant patients. Typically the breath period (BP), breath rate and expiratory time (TE) is slow enough for the CO2 signal 100 from the capnometry sensor to register the full amplitude of the actual CO2 102 in the breath sample, and an accurate etCO2 result is reported. The capnometry curve can be broken down into 7 parts. The inspiratory part 1 of the breathing curve, during which there is basically no signal response from the Capnometer; the beginning of exhalation 2 during which again there is basically no signal response from the Capnometer; a sensor lag time 3 which is a brief lag period or delay before the sensor responds to the first CO2 gas molecules in the exhalation gas seen by the sensor's sensing element; an increasing signal in the middle of exhalation 4 due to the increasing percentage 5 of CO2 being expelled as gas from deeper in the lung is expelled; a plateau 6 representative of alveolar gas and when the sensor has had time to fully respond to the concentration of CO2 molecules; and the, a lag time or delay 7 from the sensor responding to a drop in the CO2 level when exhalation ends and inspiration begins; and a drop 8 in the signal corresponding to the response time of the sensor reacting to no CO2. The differences between the "Actual CO2" curve 102 and the "Capnometry Signal" curve 100 demonstrate the effects that the response time of the sensor has on the sample measurement. These effects can be subtle and unimportant in many clinical applications, but in others, such as neonatal applications, these effects can be detrimental. Below the graph the sections of gas that is being drawn from the patient, in the case of side stream monitoring, is shown graphically as inspired ambient air 110, expired airway air 112, and expired alveolar air 114.

Figure 2:
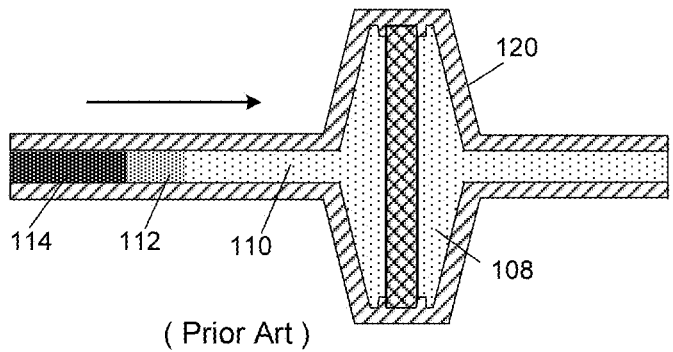
FIG. 2 describes a side view cross section of a prior art filter used for filtering gas collected from a patient.
Figure 3:
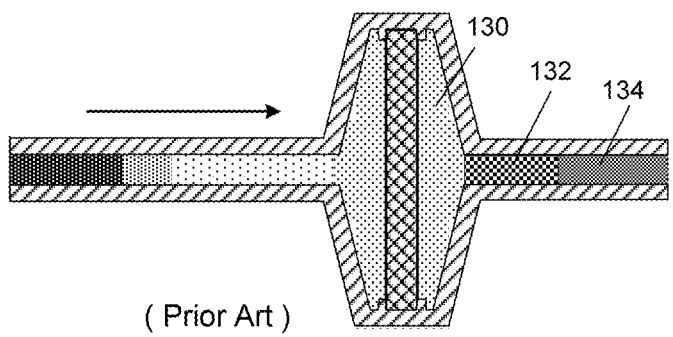
FIG. 3 describes the prior art filter of FIG. 2 showing the mixing of gas sections that occurs as gas travels through the filter.

In FIGS. 2 and 3, the problem of mixing of expiratory alveolar gas with non-alveolar gas is exemplified. The effect of an in-line filter is shown as an example. Such a filter is often used tp filter humidity or bacteria from the patient along a section of sampling tubing that is being used to draw the sample from the patient. In FIG. 2, the different primary breath gas sections (alveolar 114, upper airway 112 and ambient 110) are shown moving in packets along the sampling pathway 122 to the inlet of a filter 120. The gases from a first breath are shown entering the filter. The filter has presumably previously been purged and filled with ambient air, or simply as ambient air inside as baseline condition, and thus is shown filled with ambient air 108, as is the conduit on the outlet side of the filter. In FIG. 3, as the different gas sections from the patient's first breath, inspired ambient air 110, airway air 112 and alveolar air 114, travel through the filter, the sections mix with the ambient air in the filter to create mixed gas 130, and exit the filter diluted with the ambient air to create a contaminated airway air sample 132 and a diluted end-tidal sample 134. After a number of breaths, if the breathing pattern is steady state, the dilution reaches a steady state, but the result is that the incoming sample is diluted or contaminated in the filter and exits the filter no longer in its pure original state. The solution to this problem is described in a separate Capnia patent application No. 61/872,270, the entire contents of which are incorporated herein.

Figure 4:
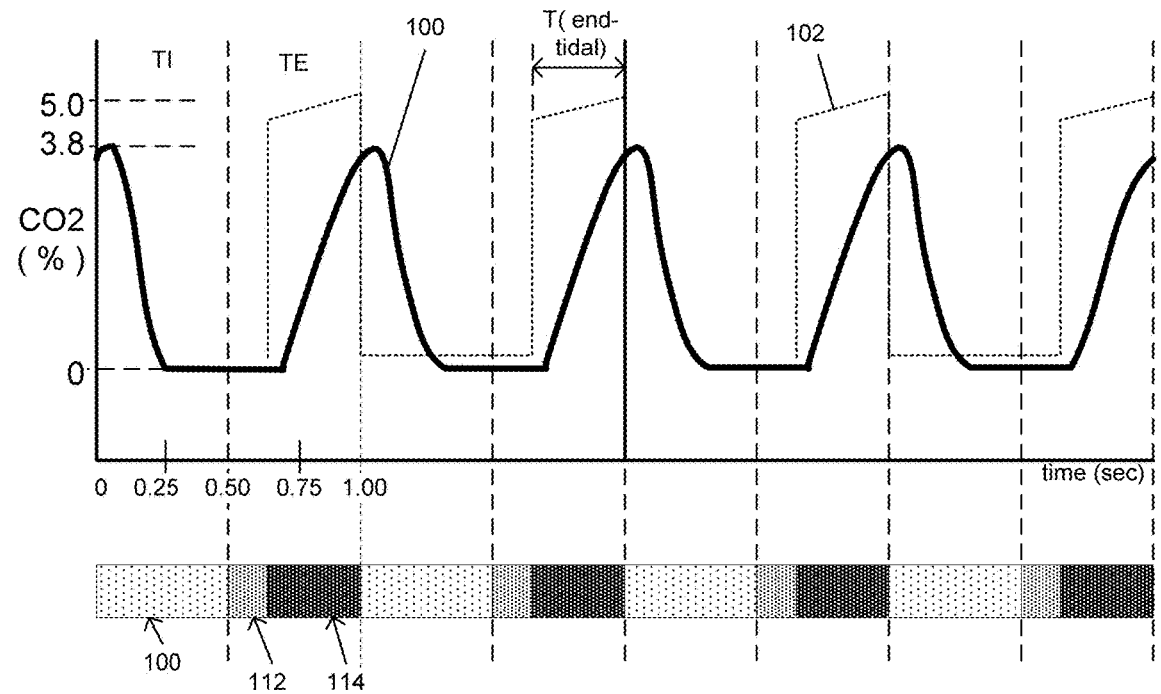
FIG. 4 graphically shows the capnometry signal for a series of breaths as a function of time, in which the Capnometer is not able to measure the true peak value of the CO2 in the patient's breath, the subject of which the present disclosure solves.

FIG. 4 shows the problem of sensor signal response time, and the potential inability of the sensor to measure the peak gas level. Again in this case capnometry is used as an example, but the measurement can be other analytes. The breath rate shown is 60 bpm. The alveolar gas exhalation time is approximately 250-275 msec. The sensor response time is >275 msec. The peak sensor signal registers 3.8%, while the actual peak percentage is 5.0%. Hence, this system is not capable of measuring CO2 under these clinical conditions. Now turning to the rest of the figures, the solution to the problem described in FIG. 4 is described.

In FIGS. 5 through 14, a new breath gas sampling and measurement system is described. In order to overcome the response time limitation, the system stores the appropriate section of exhaled gas from more than one breath, then the system sends the multiple-sample bolus through the sensor. For example, if the bolus may be composed of end-tidal gas samples from two breaths, each of 150 msec in duration, the resultant combined sample therefore being of 300 msec in duration. With this unique design and method, the sensor has enough time to register the full amplitude of the CO2 in the bolus, now that the bolus is 300 msec long, rather than only 150 msec long.

Figure 5:
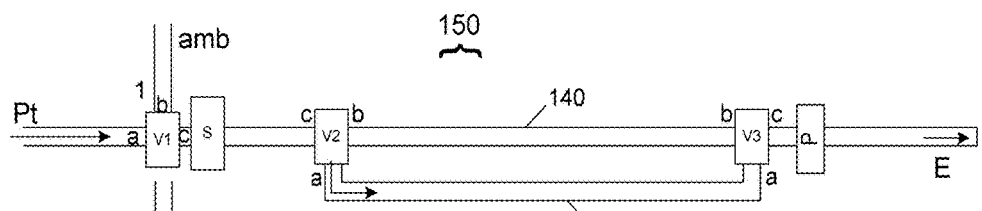
FIG. 5 describes a schematic of a pneumatic system of the present disclosure used to collect and measure patient gas.
Figure 6:
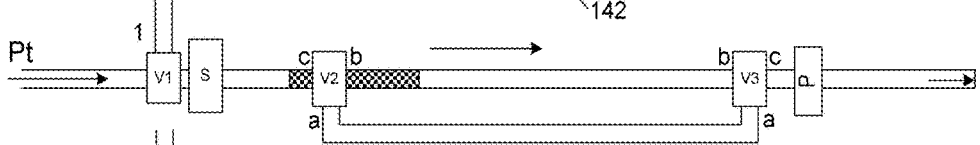
FIG. 6 describes the system of FIG. 5 in which a desired section of gas, for example the end-tidal section, is shunted into an isolation chamber to isolate it from other gases.
Figure 7:
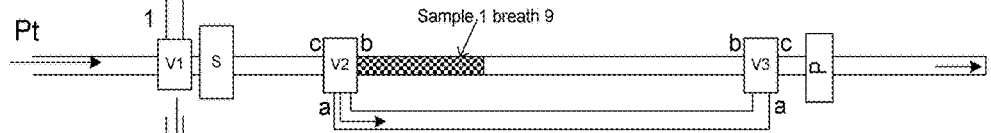
FIG. 7 shows the system of FIGS. 5-6 wherein the desired sample is fully placed in the isolation chamber and lined up precisely with the inlet to the chamber.
Figure 8:
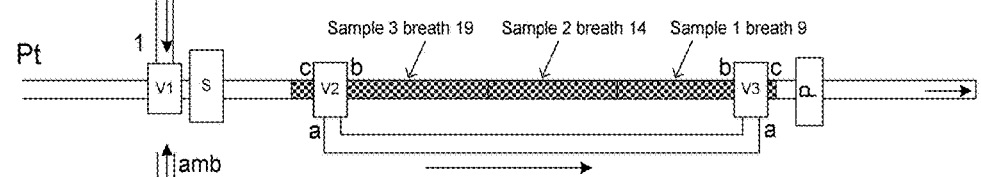
FIG. 8 shows the system of FIGS. 5-7 in which desired sections of gas from three separate desired breaths are shunted into the isolation chamber to fill the chamber, without space in-between the sections.
Figure 9:
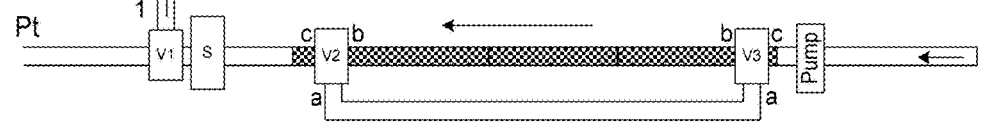
FIG. 9 shows the system of FIGS. 5-8 in which the gas sample bolus in the isolation chamber is diverted to a sensor for measurement.

In FIG. 5, the pneumatics of the apparatus 150 are described, comprised of a patient inlet Pt, an inlet valve V1, an ambient inlet amb, a breath analyte sensor S, a sample collection compartment 140, a bypass channel 142, a valve V2 at the inlet to the sample collection compartment, a valve V3 at the opposite end of the sample collection compartment, a pump P, and an exhaust E. The valves V1, V2 and V3 each may have three ports, a, b, and c, with c port always open, and the system toggling between ports a and b during the collection and test sequence. In FIG. 5 gas from the patient is being drawn into the apparatus by a vacuum pump P, through for example a nasal cannula or sampling tube attached to the patient inlet Pt of the apparatus. The patient gas travels around the sample collection area 140 through the bypass 142 (valve V2 port b to valve V3 port b) until an end-tidal sample from a targeted breath is identified by the sensor S and arrives at valve V2. At this time, shown in FIG. 6, the end-tidal sample is allowed into the sample collection area 140, and when it is properly aligned and positioned in that area, the patient gas is once again diverted around this area through the bypass, shown in FIG. 7. Eventually, the sample collection area is filled with two or more end-tidal samples from two or more breaths, as shown in FIG. 8. Finally, as shown in FIG. 9, the pump direction is reversed, the patient inlet is closed at Valve V1 and the ambient port amb is open, and the sample bolus is pushed back through the sensor S with ambient air stemming from the exhaust E behind it, and out the ambient port b of valve V1. The sensor S measures the CO2 in the sample bolus as it traverses through it, thus registering a etCO2 value.

Figure 10:
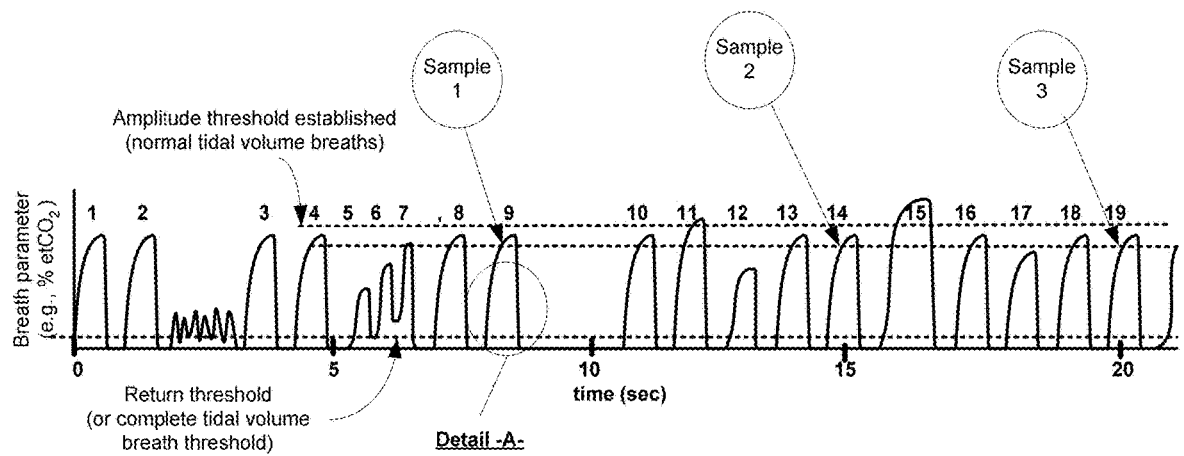
FIG. 10 shows a CO2 breath waveform diagram as a function of time for a series of breaths and threshold criteria for selection and disqualification of breaths to be chosen for analysis.

Now referring to FIG. 10, the breaths from which the multiple end-tidal samples are collected can be from non-consecutive breaths, in the event of non-steady-state breathing, or episodic breathing, or erratic breathing. Breath pattern algorithms are employed to target breaths that are representative of a certain breath type, for example normal tidal volume breaths, and to exclude other breaths, so as to obtain a sample bolus that is truly homogenous of the type of breath being sought for measurement. Breath measurement thresholds and other breath criteria are defined, either prospectively, in real time, or retrospectively, or combinations thereof, to establish what is normal and not normal for the particular situation. As shown in FIG. 10, breaths 9, 14, and 19 pass the criteria and are deemed acceptable and are targeted for sample collection. Returning to FIG. 8, the end tidal gas samples from these three targeted breaths are shown collected and stored in the sample compartment 140.

Figure 11:
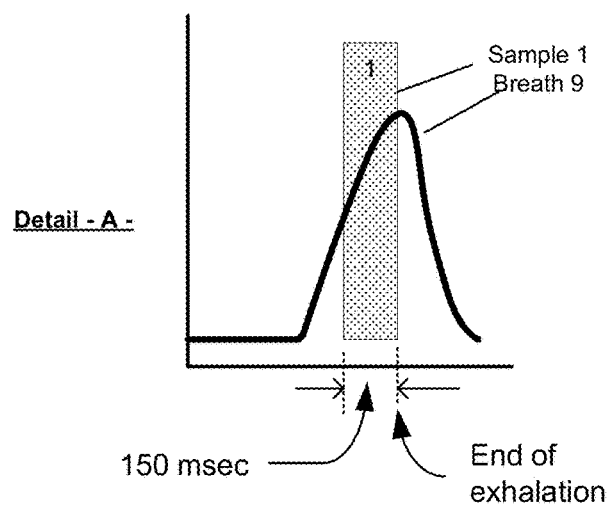
FIG. 11 shows a close up view of a breath waveform from the series of breaths shown in FIG. 10.
Figure 12:
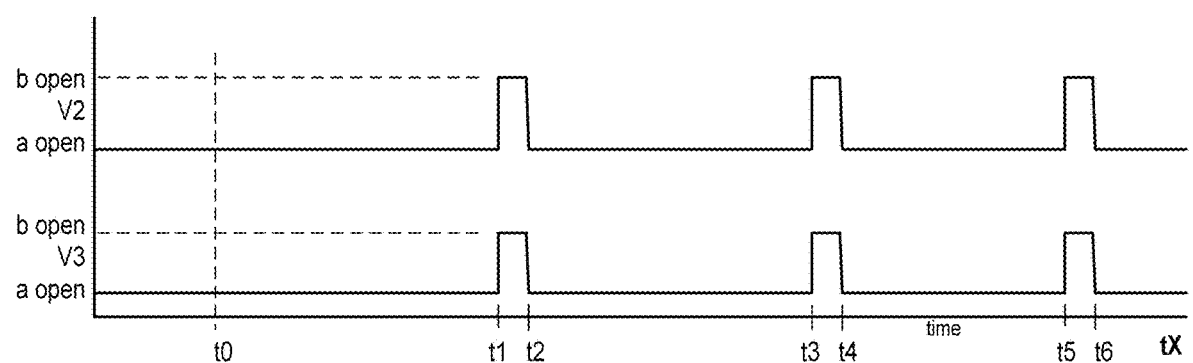
FIG. 12 shows a timing diagram of the valve operation of the system in FIG. 5 for the purpose of collecting and isolating the desired end-tidal samples from the desired breaths shown in FIG. 10.
Figure 13:
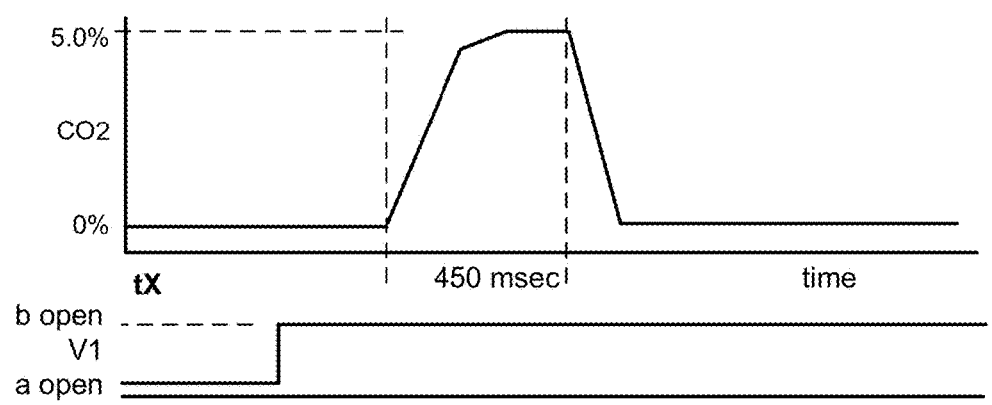
FIG. 13 graphically shows the sensor CO2 signal of the sample bolus from the system in FIG. 9 and from the breaths shown in FIG. 10 when measured by the sensor, along with a valve timing diagram on the same time scale indicating the valve operation of the system in FIG. 9.

In FIG. 11, breath 9 from FIG. 10 is shown in more detail. It is desired in this example to acquire and measure the last 150 msec of an exhaled breath from more than one breath. The last 150 msec will assure that the sample is a deep lung sample and representative of what is in the blood, even at very fast breath rates. This time can be a default value, or can be configurable automatically or manually, based on the clinical application, and/or the prevailing breathing pattern. FIG. 12 describes the timing and operation of the valves V2 and V3 in FIGS. 5-8 in order to shunt, isolate and store these samples in the sample collection area, and to prevent mixing of these samples with other gases, in order to assure a homogeneous sample bolus of end-tidal deep alveolar gas of sufficient volume. It may be advantageous to control the valves such that the end-tidal samples of the first and last breath that are targeted overflow the sample collection area; the beginning of sample 1 extends out of the sample collection area, and the end of sample 3 does not quite enter the sample collection area. This "overfilling" technique will help assure that the sample collection area does not contain any non-end-tidal sample, which could act to contaminate the concentration of the targeted gas in sample. FIG. 13 shows the valve timing and operation of the operational step shown in FIG. 9, when the end-tidal sample bolus is sent back to the sensor, as well as the sensor's corresponding signal response to the sample bolus. As can be seen, the sensor now has ample time to respond to the analyte level in the bolus, and an accurate measurement is made and can be reported. In FIGS. 11 through 13, 150 ms is the time duration of the desired and selected sample to be captured (the last 150 msec of exhalation), t0 is the time that the end-of-exhalation of the first good sample exits the sensor S, t1=t2−150 msec, t2=t0+Xxmsec, XXmsec is time for gas to travel from sensor S outlet to V2 inlet.

Figure 14:
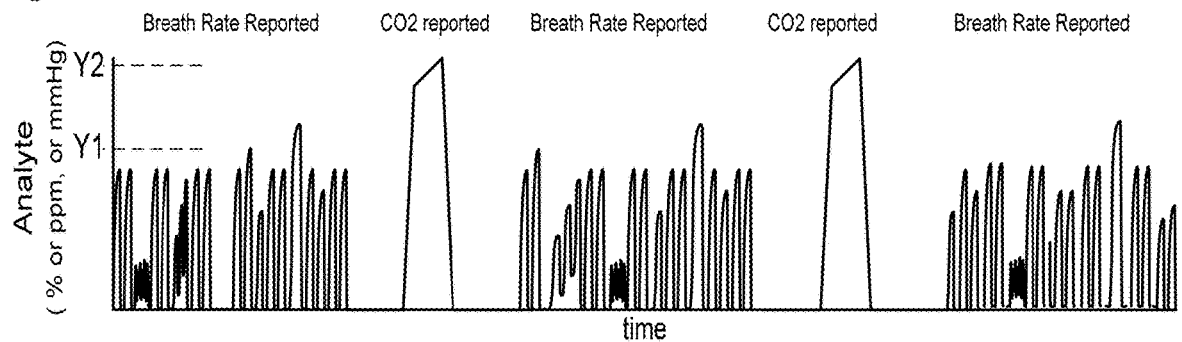
FIG. 14 graphically shows the use of an exemplary apparatus as a function of time, with breath rate reporting interspersed by CO2 level reporting, and repeating.

In FIG. 14, an example of using an exemplary embodiment is shown. For example a breath rate can be reported using the "clipped" capnometry signal. This can take place for example for one minute, during which time the multiple end-tidal samples from multiple targeted breaths are being collected and stored. Then, after that one minute period, breath rate reporting can be temporarily interrupted for about 3-15 seconds during which time the end-tidal sample bolus is shuttled to a CO2 sensor, and the CO2 level can be reported by the methods described earlier. Then, the above sequence is repeated, such as; breath rate reporting for one minute, 10 second period for etCO reporting, breath rate reporting for one minute, 10 second period for etCO reporting.

Figure 15:
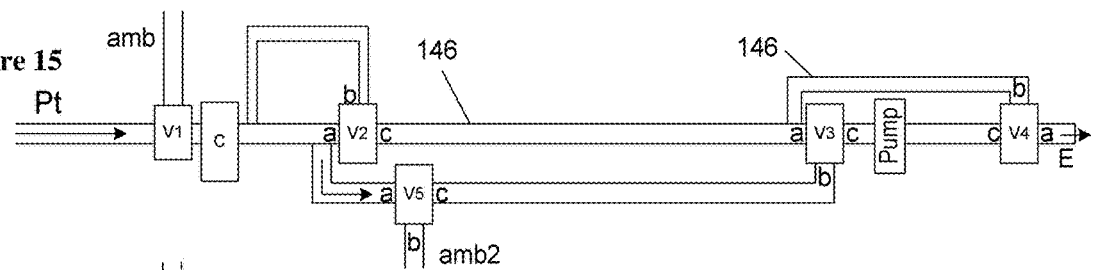
FIG. 15 shows a pneumatic schematic of an alternate pneumatic configuration, in which the sample bolus after collection is diverted to a sensor for measurement without changing the direction of the flow generator.
Figure 16:
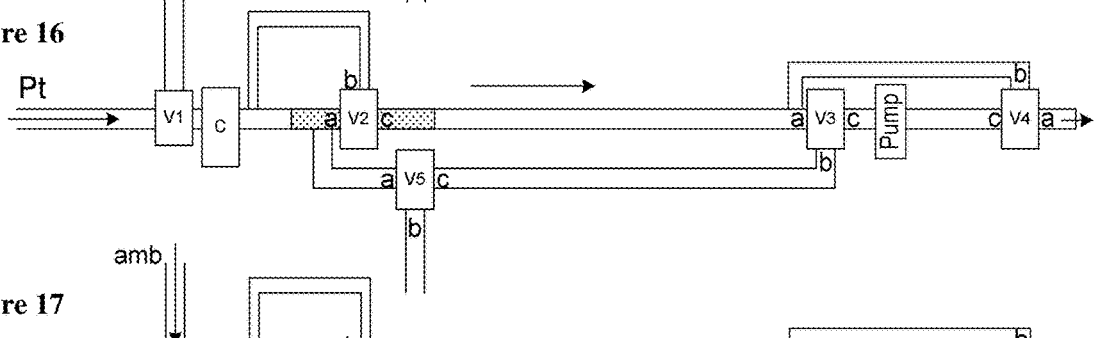
FIG. 16 shows the system of FIG. 15 with a first sample from a first selected breath entering a sample isolation chamber.
Figure 17:
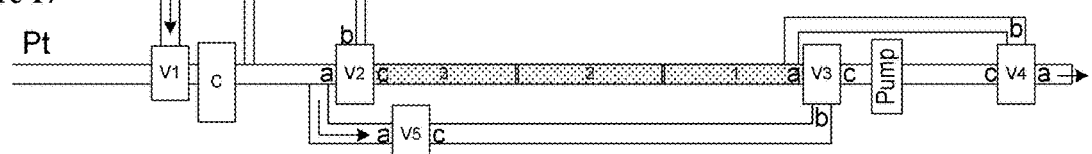
FIG. 17 shows the system of FIGS. 15 and 16, with several samples from several selected breaths now occupying the sample isolation chamber.
Figure 18:
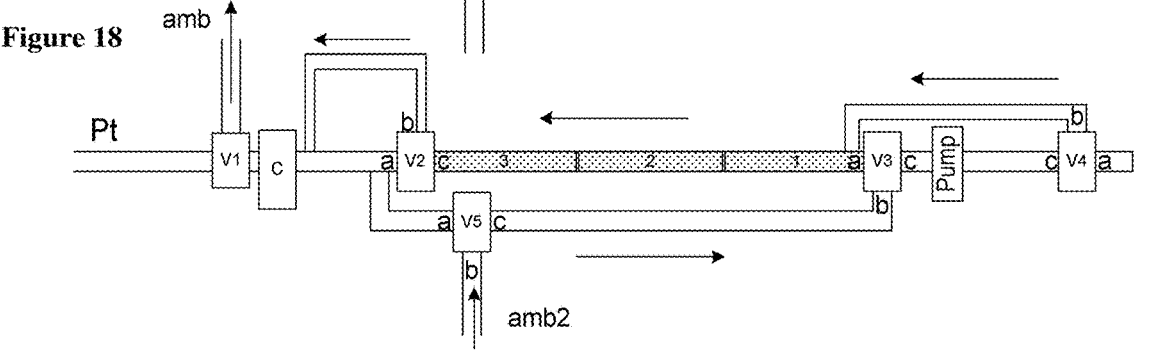
FIG. 18 shows the system of FIGS. 15-17 in which the sample bolus is diverted to a sensor for compositional analysis.
Figure 19:
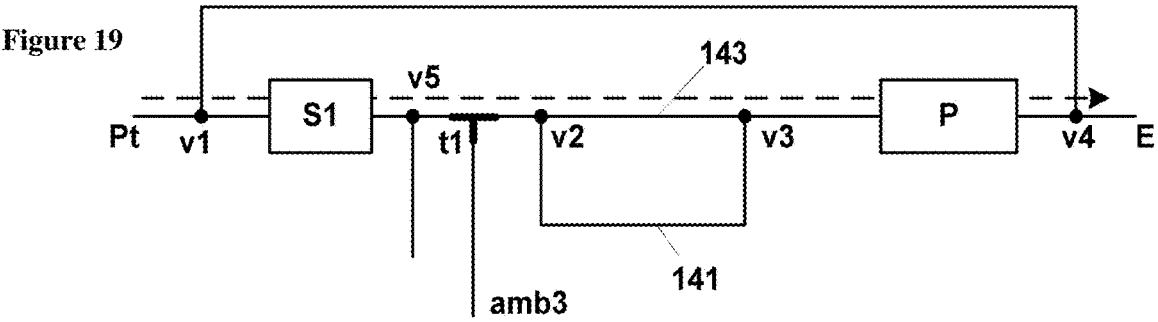
FIG. 19 shows a pneumatic diagram of an alternate pneumatic configuration in which the flow generator direction remains constant, and shows the state in which flow from the patient is being drawn through the system.

FIGS. 15 through 18 describe an alternative pneumatic sampling and measurement system. In this alternative, the pump direction need not be reversed, which may be beneficial with certain types of pump technologies, and to guarantee smooth, consistent pump speed and gas flow rate operation. In FIG. 15 the apparatus comprises an additional inlet valve V5 coupled to the bypass tube 142, V5 with an ambient inlet port amb 2, a reverse flow valve V4, a push tube 144, and a reverse tube 146. As shown in FIG. 15, gas from the patient enters the system through the patient inlet Pt, through valve V1, sensor C, valve V5, valve V3, pump P, valve V4 and out exhaust E. As shown in FIG. 16, when a breath desired for sampling is identified, V2 and V3 switch to shunt the end-tidal sample into the sample collection tube 140. The identified and targeted multiple end-tidal samples are collected and properly aligned and positioned in the sample collection area similar to that describe in FIGS. 5-9. As shown in FIG. 17, Valve V1 is then switched to the amb inlet so that the patient gases in the various sections of gas pathways other than the sample collection area are purged by ambient air being drawn in through Valve V1, through C, V5, the bypass tube 142, V3, the pump P and V4. After purging the system, V2, V3, V4 and V5 switch as shown in FIG. 18, so that ambient air is now drawn in from V5 port b, drawn through V3 port b and the pump, and pushed through V4 port c and b into the sample collection area to push the sample bolus through V2 port c and b, and through the Sensor C, and out V1 to ambient air. It should be noted that the systems described herein can include a single sensor for performing both (a) the initial breathing pattern measurements and sample targeting, and (b) analyte measurement in the multi-sample bolus, or can include more than one sensor, for example one for (a) and a second sensor for (b).

Figure 20:
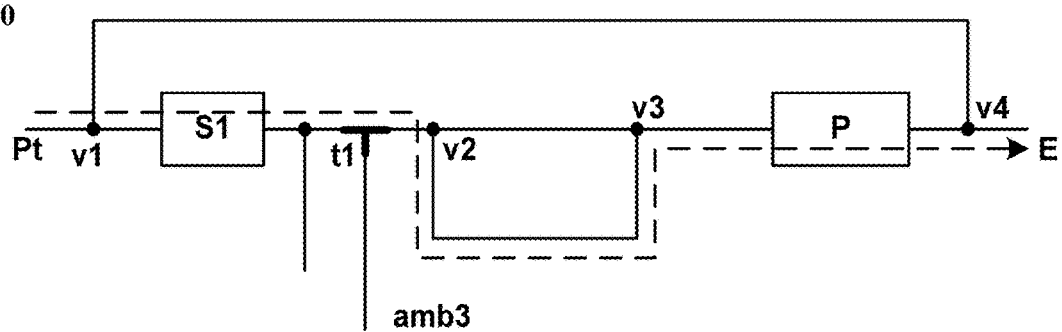
FIG. 20 shows the system of FIG. 19 in which gas is diverted to a second branch for the purpose of shunting and storing a desired sample of gas from a desired breath.
Figure 21:
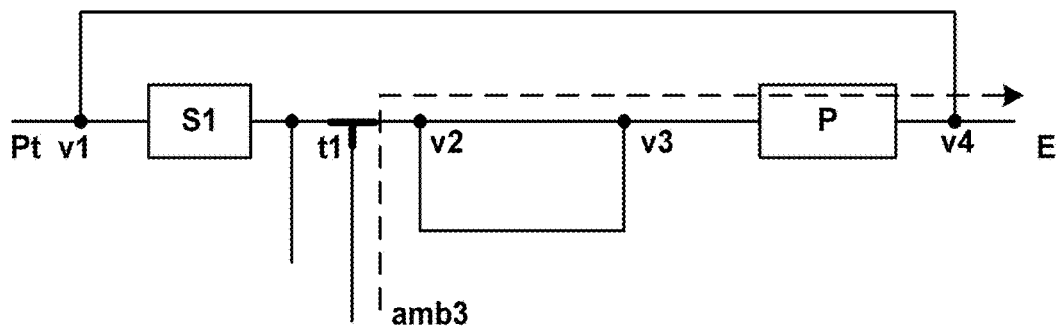
FIG. 21 shows the system of FIGS. 19 and 20 in which ambient air is drawn into the system to flush out residual unwanted patient gases.
Figure 22:
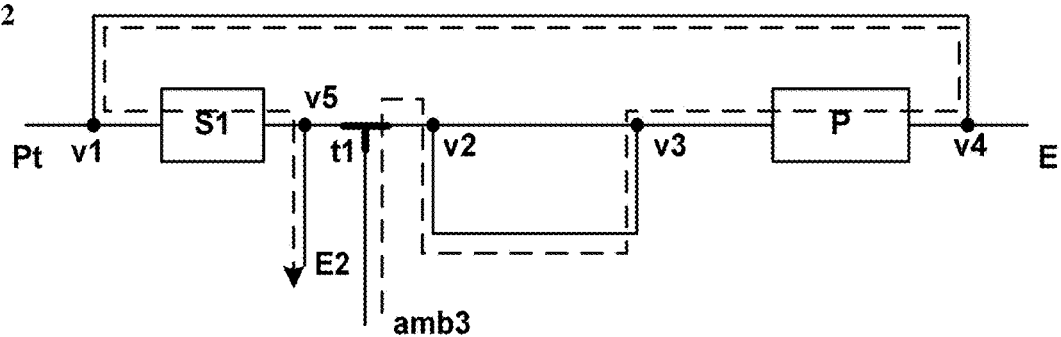
FIG. 22 shows the system of FIGS. 19-21 in which ambient air is drawn in to divert the sample bolus to a sensor for measurement and out another ambient port for exhausting out of the system.

FIGS. 19-22 show an additional pneumatic configuration. As shown if FIG. 19 patient gas flows in through Pt, v1, S1, v5, t1, v2, v3, P, v4 and out E. As shown in FIG. 20, when an end-tidal sample from a targeted breath reaches v2, the valves v2 and v3 are switched to allow the end-tidal sample into the sample collection tube, 141, then the valves are switched back to allow flow through segment 143, thus isolating the end-tidal sample. Then as shown in FIG. 21, after the sample collection tube 141 is sufficiently filled with end-tidal gas from multiple samples, ambient air is drawn in through valve t1 from the ambient inlet amb3, to purge parts of the system of unwanted patient gas sections. The, in FIG. 22, ambient air from amb3 is used to push the end-tidal sample bolus to v1 via v4, v3, v2 and t1, and through the sensor S1 and out the exhaust E2 via v5.

It should be noted that while different pneumatic branching structures and different combinations and locations of valves and pumps are contemplated, a common theme is that the end-tidal samples must be stored until enough end-tidal sample is collected, and that the time durations of each of the captured end-tidal samples, when added together, must add up to a time duration that is at least close to, preferably equal to, and most preferably greater than, the signal response time of the sensor that is being used to measure the gas in the sample bolus.

The system described herein can be useful for collecting and measuring end-tidal gas samples, as well as samples from other sections of the breath. It can be used for measuring for example CO2 in the breath, or other gases, such as CO, H2, NO, and others. It can be used for measuring other non-gaseous substances in the breath as well as gaseous markers. The system disclosed can be used for period, intermittent, semi-continuous, or continuous measurements and monitoring. While overcoming fast breathing patterns is used throughout the foregoing descriptions, the disclosure can be applied to overcome other breathing pattern challenges.

What is claimed is:

1. A method of measuring a breath analyte using a gas sampling and analysis system comprising:
    drawing a series of breaths into the system through a nasal cannula;
    monitoring the series of breaths with a single analyte sensor of the system;
    determining a plurality of breath segments of the series of breaths to capture, wherein each of the plurality of breath segments comprises a duration shorter than an analyte response time of the single analyte sensor;
    collecting the plurality of breath segments together in a multiple sample bolus;
    reversing or directing flow of the multiple sample bolus through the single analyte sensor used to monitor the series of breaths, and then out to ambient air; and
    measuring an analyte concentration of the multiple sample bolus using the single analyte sensor, wherein the reversed or directed flow of the multiple sample bolus comprises a duration longer than a response time of the single analyte sensor.

2. The method of claim 1, wherein monitoring the series of breaths comprises monitoring a breath rate of the series of breaths.

3. The method of claim 1, wherein monitoring the series of breaths comprises monitoring a capnometry signal of each breath.

4. The method of claim 1, wherein determining a plurality of breath segments of the series of breaths to capture comprises identifying breaths with a normal end-tidal profile.

5. The method of claim 1, wherein determining a plurality of breath segments of the series of breaths to capture comprises excluding one or more of a non-steady state breath, an episodic breath, and an erratic breath.

6. The method of claim 1, wherein the breath analyte is $CO_2$.

7. The method of claim 1, wherein the single analyte sensor is an infrared $CO_2$ sensor.

8. The method of claim 1, wherein each of the plurality of breath segments has a duration of 150 msec.

9. The method of claim 1, wherein the breath analyte is H2.

10. The method of claim 1, wherein the breath analyte is nitric oxide.

11. A system for measuring a breath analyte comprising:
    a nasal cannula for drawing a series of breaths into the system;
    a single analyte sensor that generates data from the series of breaths;
    a processor that receives the data and determines a plurality of breath segments of the series of breaths to capture based on the data, wherein each of the plurality of breath segments comprises a duration shorter than an analyte response time of the single analyte sensor;
    a chamber that collects the plurality of breath segments together in a multiple sample bolus; and
    a pump that reverses or directs flow of the multiple sample bolus through the single analyte sensor that generates data from the series of breaths,
    wherein the single analyte sensor measures an analyte concentration of the multiple sample bolus, and wherein the multiple sample bolus comprises a duration longer than a response time of the single analyte sensor.

12. The system of claim 11, wherein the single analyte sensor generates data on a capnometry signal of each breath of the series of breaths.

13. The system of claim 11, wherein the processor determines the plurality of breath segments of the series of breaths to capture by identifying breaths with a normal end-tidal profile.

14. The system of claim 11, wherein the processor determines the plurality of breath segments of the series of breaths to capture by excluding one or more of a non-steady state breath, an episodic breath, and an erratic breath.

15. The system of claim 11, wherein the breath analyte is $CO_2$.

16. The system of claim 11, wherein the single analyte sensor is an infrared $CO_2$ sensor.

17. The system of claim 11, wherein each of the plurality of breath segments comprises a duration of 150 msec.

18. The system of claim 11, wherein the breath analyte is H2.

19. The system of claim 11, wherein the breath analyte is nitric oxide.

* * * * *